United States Patent [19]

Christensen

[11] Patent Number: Plant 5,705

[45] Date of Patent: Apr. 1, 1986

[54] HYBRID TEA ROSE CV. AROGRESH

[75] Inventor: Jack E. Christensen, Ontario, Calif.

[73] Assignee: Armstrong Nurseries, Inc., Ontario, Calif.

[21] Appl. No.: 640,100

[22] Filed: Aug. 13, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Synnestvedt & Lechner

[57] ABSTRACT

A new hybrid tea rose of the tall bush type, cultivated for garden decoration. The new cultivar bears unusually colored yellow-green flowers with light touches of soft pink. Its blossoms are extremely long-lived in the garden, often lasting over seven days. The yellow-green flower coloration intensifies as the blossoms age on the bush. Flowers are produced on long, cutting-length stems. The plant bears an abundance of dark green, semi-glossy leathery foliage and displays an above-average resistance to mildew, rust and blackspot.

1 Drawing Figure

This invention relates to a new variety of hybrid tea rose cv. Arogresh. The plant is an outdoor seedling of the tall bush type, cultivated for garden decoration. The plant's hardiness is as yet untested. It was first discovered and asexually reproduced by Jack E. Christensen in Ontario, Calif., having as its seed parent White Masterpiece (U.S. Plant Pat. No. 2,998), and as its pollen parent Queen Elizabeth (U.S. Plant Pat. No. 1,259).

The new rose cv. Arogresh is particularly distinguishable from other commercialized rose cultivars by the following combination of characteristics: the unusual coloration of its flowers, yellow-green with light touches of soft pink; the extremely long life—often more than seven days—of its flowers in the garden; the intensifying of its yellow-green flower coloration as the blossoms age on the bush; the plant's inability to set hips, which insures continual flower production under Ontario, Calif. growing conditions during the blooming period without requiring the removal of dead blooms; its abundant, dark green, semi-glossy leathery foliage; and its long cutting stems and upright growth. The new variety holds its distinguishing characteristics through succeeding propagations by budding.

The new rose cultivar Arogresh may be distinguished from its seed parent, White Masterpiece (U.S. Plant Pat. No. 2,998), by the following combination of characteristics: White Masterpiece produces flowers of a relatively uniform white coloration, whereas the new cultivar produces flowers of an unusual yellow-green and pink combination, essentially as described and illustrated herein. Arogresh produces flowers of 3½ to 4 inches in diameter, whereas the seed parent produces significantly larger blooms of 5 to 6 inches in diameter. Whereas White Masterpiece produces a mature bush of medium-low height, the new rose produces a significantly taller mature bush under Ontario, Calif. growing conditions.

Arogresh may be distinguished from its pollen parent, Queen Elizabeth (U.S. Plant Pat. No. 1,259), by the following combination of characteristics: Queen Elizabeth produces flowers of a relatively uniform pink coloration, whereas the new cultivar produces flowers with a coloration of yellow-green and pink, essentially as described and illustrated herein. Arogresh produces blooms with 30 to 35 petals, whereas the pollen parent produces blooms of significantly heavier petalage (37 to 40 petals). Queen Elizabeth will readily set hips under Ontario, Calif. growing conditions, whereas the new rose will not set hips under similar conditions.

The accompanying drawing illustrates the new variety in color as grown in Ontario, Calif., and shows the flowering thereof from bud to full bloom.

Throughout this specification, color names beginning with a small letter signify that the name of that color as used in common speech is aptly descriptive. Color names beginning with a capital letter designate values based on The R.H.S. Colour Chart published by The Royal Horticultural Society of London, England.

The descriptive matter which follows pertains to roses grown in Ontario, Calif. and is believed to apply to similar conditions of soil and climate elsewhere.

FLOWER

The new variety sometimes bears its flowers singly, sometimes three to four to a stem, in irregular clusters on strong stems that are medium to long in length for the class. Outdoors, flowers are produced in abundant quantities and nearly continuously throughout the growing season. The flowers have a slight tea fragrance.

BUD

The peduncle is of average length for the class, of average to heavy caliper, strong, erect, and stiff. It is moderately smooth with numerous stipitate glands and few small prickles. The peduncle is between Yellow-Green 144A and Green 137B in color.

Before the calyx breaks, the bud is medium to large in size for the class, medium to long in length, and pointed to ovoid in form. There are few stipitate glands on the surface of the bud. There are usually slender, entire foliaceous parts present which extend beyond the tip of the bud a distance equal to one quarter or more of the length of the bud.

As the calyx breaks, bud color is between Yellow-Green 144D and Greyed-Yellow 160C; petal tips are sometimes speckled with near Red 39A. The inner surface of the sepals has a fine, woolly tomentum; margins are lined with stipitate glands and hairs.

As the first petal opens, the bud is average in size for the class, medium to long in length, and pointed to ovoid in form. On their outside surface, the petals display a color between Yellow-Green 145C and Greyed- Yellow 160C; petal edges are lightly blushed with between Red 36A and Red 36C. The inner surface of the petals is the same color as the outside surface with a broader band of blushing on the petal edges. The bud opens up well and is not prevented from opening by cold, hot, wet, or dry weather.

BLOOM

When fully open, the bloom is average in size for the class, from 3½ to 4 inches in diameter. The petalage is double with petals arranged regularly; petals number from 30 to 35, and there may be 1 to 4 petaloids present. Bloom form when half open is moderately high-centered to cupped, with petals moderately spiraled to cupped and with petal edges somewhat reflexed outward. When fully open, the bloom is moderately cupped in form, with petals more cupped and with petal edges somewhat flat to slightly undulated and reflexed outward.

Petals are of moderately heavy substance and medium thickness, slightly satiny to velvety inside and slightly shiny outside. Outside petals are nearly round with flat to rounded apices and are sometimes scalloped. Intermediate petals are broadly obovate with rounded to sometimes notched apices. The inside petals are obovate with rounded apices; these are sometimes notched. Colors of all petals may be modified by being bordered or margined or blotched or shaded or washed or tinted with other colors.

The following paragraph describes the color values observed in a newly opened flower from a plant of the new variety grown outdoors in Ontario, Calif. during the month of October.

The outside surface of the outside, intermediate and inside petals has a coloration between Yellow-Green 145C and Greyed-Yellow 160C, with petal edges very lightly bordered with between Red 36A and Red 36C. The inside surface of the outside petals has the same coloration as the outside surface of the outside petals. The inside surface of the intermediate and inner petals is the same color as the outside surface of the outside petals with the addition of a broader band of bordering at the petal edges.

The following paragraph describes the color values observed in a flower that had been open for three days on a plant grown outdoors in Ontario, Calif. during the month of October.

The outside surface of the outside and inside petals and the inside surface of the outside petals have a color between Yellow-Green 145B and Greyed-Yellow 160C. The inside surface of the inside petals has the same coloration as the outside surface of the outside petals, except that the petal edges on the inside surface of the inside petals are sometimes very lightly bordered with near Red 36D.

The general color effect of a newly opened flower is between Yellow-Green 145C and Greyed-Yellow 160C, with petal edges bordered with between Red 36A and Red 36C toward the center of the flower. The general color effect of a flower that has been open three days is between Yellow-Green 145B and Greyed-Yellow 160C.

Petals usually persist and are not particularly affected in this respect by cold, hot, wet, or dry weather. Flowers last 5 or more days on the bush in the garden during the month of October. Flowers cut from plants grown outdoors in the month of October will last from 6 to 7 days at living-room temperatures.

REPRODUCTIVE ORGANS

Stamens are few to average in number and are arranged regularly about the pistils. Filaments are short to medium in length and most have anthers; the anthers are of medium size, and all open approximately at once. Anther color is near Yellow 8C when immature; color of the mature anthers is near Greyed-Orange 165A. Pollen is somewhat sparse and has a color near Yellow 8D.

There are many pistils (approximately 70). Styles are uneven, very short to average in length, of average caliper and somewhat loosely bunched. Stigma color is near Green-Yellow 1D.

This variety does not normally set hips under Ontario, Calif. growing conditions.

FOLIAGE

The compound leaves usually comprise from 3 to 5 leaflets and are borne in abundant amounts. Leaves are medium to large in size for the class and are very heavy to somewhat leathery and semi-glossy. Leaflets are nearly oval in shape with acute apices and round bases; their margins are simply serrate.

The color of the upper surface of the mature foliage is between Yellow-Green 147A and Green 139A; the under surface is between Yellow-Green 147C and Green 136C. The color of the upper surface of the young foliage is the same as the color of the upper surface of the mature foliage, washed with between Greyed-Purple 187A and Greyed-Purple 183A. The under surface of the young foliage is the same color as the under surface of the mature foliage, washed with between Greyed-Purple 187B and Greyed-Purple 183B.

The rachis is average in size to heavy; its upper side is grooved with some stipitate glands on the edges. The underside of the rachis is moderately smooth and bears stipitate glands.

Stipules are moderately long, of narrow to medium width, and have short points turning out at an angle of less than 45°.

The plant displays a more-than-average resistance to mildew, rust and blackspot as compared to other cultivars now in commerce grown under comparable conditions at Ontario, Calif.

GROWTH

Plants of the new variety are much-branched, bushy, tall and upright. Canes are medium to heavy in caliper for the class, and plant growth is moderately vigorous.

The main stems are between Yellow-Green 146D and Green 138B in color. They bear several large prickles of medium length for the class which are almost straight, hooked slightly downward, with moderately long, broad bases. Large prickle color is near Greyed-Orange 165A. There are no small prickles and no hairs.

Branches are between Yellow-Green 146B and Green 137B in color. They bear several large prickles of medium length for the class which are almost straight, hooked slightly downward, with moderately long, broad bases. Large prickle color is near Greyed-Orange 166C. There are no small prickles and no hairs.

New shoots have the same color as the branches, washed lightly with between Greyed-Purple 187A and Greyed-Purple 183A. The new shoots bear several large prickles of medium length for the class which are almost straight, hooked slightly downward, with moderately long, broad bases. Large prickle color is near Greyed Purple 183C. There are no small prickles and no hairs.

I claim:

1. A new and distinct variety of rose plant of the hybrid tea class, essentially as described and illustrated herein, being particularly characterized by the unusual coloration of its flowers, yellow-green with light touches of soft pink; the extremely long life—often more than seven days—of its flowers in the garden; the intensifying of its yellow-green flower coloration as the blossoms age on the bush; the plant's inability to set hips, which insures continual flower production under Ontario, Calif. growing conditions during the blooming period without requiring the removal of dead blooms; its abundant, dark green, semi-glossy leathery foliage; and its long cutting stems and upright growth.

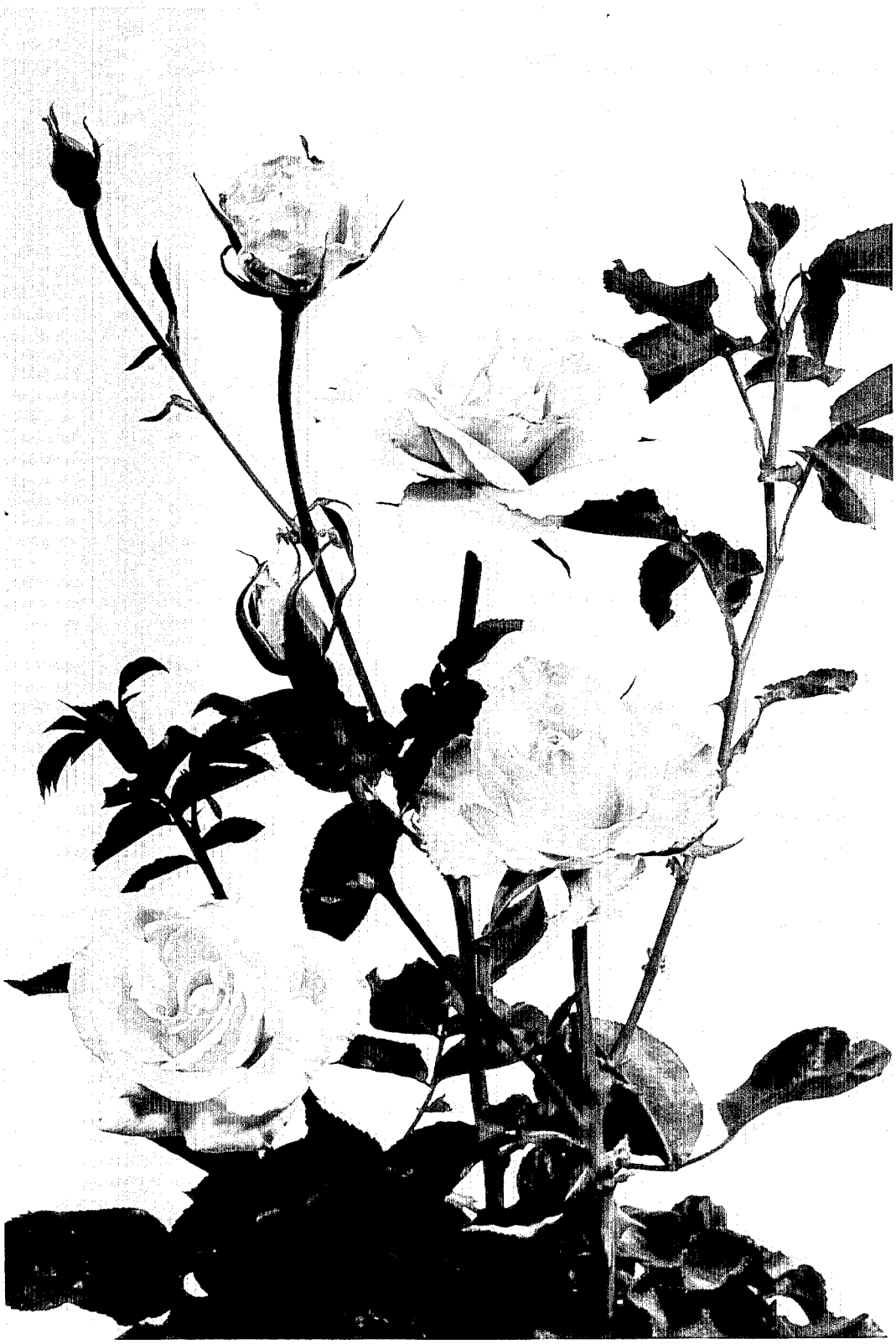

* * * * *